(12) United States Patent
Claverie et al.

(10) Patent No.: US 6,706,877 B1
(45) Date of Patent: Mar. 16, 2004

(54) METHOD FOR PRODUCING CARBOHYDRATE PARTIAL ESTERS

(75) Inventors: Valerie Claverie, Toulouse (FR); Christine Cecutti, Saint Jean (FR); Zephirin Mouloungui, Toulouse (FR); Antoine Gaset, Toulouse (FR); Catherine Le Hen Ferrenbach, Meaux (FR)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 215 days.

(21) Appl. No.: 09/402,761

(22) PCT Filed: Apr. 20, 1998

(86) PCT No.: PCT/EP98/02322

§ 371 (c)(1),
(2), (4) Date: Dec. 21, 1999

(87) PCT Pub. No.: WO98/49175

PCT Pub. Date: Nov. 5, 1998

(30) Foreign Application Priority Data

Apr. 28, 1997 (DE) .......................... 197 17 968

(51) Int. Cl.⁷ ............................... C07H 13/06
(52) U.S. Cl. ...................... 536/119; 536/124
(58) Field of Search ................. 536/119, 124

(56) References Cited

U.S. PATENT DOCUMENTS 3,996,206 A  12/1976  Parker et al. ........... 536/119 R
4,611,055 A  * 9/1986  Yamamoto et al. ......... 536/119
5,563,218 A  10/1996  Rebre et al. ................. 525/253

FOREIGN PATENT DOCUMENTS

| | | |
|---|---|---|
| DE | 11 65 574 | 3/1964 |
| DE | 20 24 051 | 12/1971 |
| DE | 41 31 505 | 3/1993 |
| EP | 0 132 941 | 2/1985 |
| EP | 0 315 265 | 5/1989 |
| EP | 0 644 211 | 3/1995 |
| GB | 962 919 | 7/1964 |
| GB | 1 333 475 | 10/1973 |
| GB | 2 256 869 | 12/1992 |
| WO | WO92/11270 | 7/1992 |

* cited by examiner

*Primary Examiner*—James O. Wilson
*Assistant Examiner*—Leigh C. Maier
(74) *Attorney, Agent, or Firm*—John E. Drach; Steven J. Trzaska

(57) ABSTRACT

A process for making carbohydrate partial esters having a degree of esterification of from 1 to 6 involving the steps of: (a) providing a catalytically active mixture containing: (i) an alkali metal carbonate; and (ii) a fatty acid lower alkyl ester; (b) providing an emulsifier mixture containing: (iii) a glycose component having from 5 to 12 carbon atoms; and (iv) a carbohydrate partial ester; and (c) combining the catalytically active mixture with the emulsifier mixture, with vigorous stirring, to form an emulsion/dispersion containing particles having a mean diameter of from 10 to 60 µm.

10 Claims, No Drawings

METHOD FOR PRODUCING CARBOHYDRATE PARTIAL ESTERS

BACKGROUND OF THE INVENTION

This invention relates to an improved process for the production of carbohydrate partial esters by transesterification of glycoses with fatty acid esters in the presence of emulsifiers and basic catalysts and to the use of the substances obtainable by the process for a number of applications.

Carbonhydrate esters, which are often also referred in short as "sugar esters", are esters of mono- or oligosaccharides and—in the broader sense—of sugar alcohols with organic or inorganic acids. Carbohydrate esters have pronounced surface-active properties so that, today, they are regarded as an independent class of compounds (so-called sugar surfactants). By virtue of their favorable dermatological and toxicological compatibility, carbohydrate esters are mainly used as emulsifiers for the production of foods and cosmetics. Sucrose polyesters containing 6 to 8 fatty acid residues could be used as a fat substitute which is not utilized by the organism in the diet of overweight people and, in addition, are said to bind LDL cholesterol in the stomach. They are normally produced by subjecting glycoses to transesterification with fatty acid methyl esters in the presence of alkaline catalysts and optionally emulsifiers. One such process is described, for example, in German patent application DE-A14131505 (Henkel). Soaps are generally used as emulsifiers for the production of the carbohydrate esters, as disclosed for example in GB-A 2,256,869.

Unfortunately, known processes are attended by the disadvantage that long reaction times are required to achieve in particular relatively high degrees of esterification, which makes the products expensive on account of the considerable reactor possession times. In addition, the products are often discolored on account of their prolonged exposure to heat. Finally, solvents often have to be used which not only adds further to the cost of the products on account of the subsequent removal of the solvents used, but also is often undesirable if the products are to be used, for example, in the food sector.

Accordingly, the problem addressed by the present invention was to provide an improved process for the production of carbohydrate partial esters which would be free from the disadvantages mentioned above.

DESCRIPTION OF THE INVENTION

The present invention relates to a process for the production of carbohydrate partial esters with a degree of esterification of 1 to 6 by alkali-catalyzed transesterification in the presence of emulsifiers, characterized in that (a) to form a catalytically active system, alkali metal carbonates are treated with fatty acid lower alkyl esters corresponding to formula (I):

$$R^1CO\text{—}OR^2 \qquad (I)$$

in which $R^1CO$ is a linear or branched, saturated or unsaturated alkyl group containing 6 to 22 carbon atoms and $R^2$ is a linear or branched alkyl group containing 1 to 5 carbon atoms, and (b) for transesterification, the resulting mixture is treated while stirring vigorously with a mixture of (b1) glycoses containing 5 to 12 carbon atoms and (b2) carbohydrate partial esters as emulsifiers, so that an emulsion/dispersion in which the particles have a mean diameter of 10 to 60 μm is obtained.

In the first step of the process according to the invention, a coating of fatty acid lower alkyl ester is formed on the alkali metal carbonate, so that the acyl group is activated. In the second step, the activated catalyst is contacted with a mixture of a glycose and a carbohydrate partial ester, the carbohydrate partial ester acting as an emulsifier. In the first step of the transesterification, acyl groups are transferred to the emulsifier which, in the further course of the reaction, itself functions as an acylating agent and transfers acyl groups to the glycose which is thus converted into a carbohydrate partial ester. The reaction takes place in the absence of solvents which is a considerable advantage not only from the economic point of view, but also with a view to the use of the end product in foods or cosmetics. Another unexpected advantage of the process is that, by virtue of the effective nature of the transesterification, the same degrees of esterification are obtained in very much shorter reaction times by comparison with the prior art.

Catalysts

Suitable catalysts are alkali metal carbonates, preferably sodium and/or potassium carbonate, which may be used in quantities of 5 to 50% by weight, preferably 10 to 20% by weight and more preferably 10 to 15% by weight, based on the fatty acid lower alkyl esters.

Fatty Acid Lower Alkyl Esters

Typical examples of suitable acylating agents are the esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof with methanol, ethanol, propanol, isopropyl alcohol, n-butanol, i-butanol, tert.butanol, n-pentanol and isopentanol. Methyl and/or ethyl esters of $C_{12-18}$ fatty acids are preferably used, the molar ratio of ester to glycose being from 1:3 to 3:1 and preferably from 1:2 to 2:1, depending on the required degree of esterification.

Production of the Catalyst System

To produce the catalyst system, i.e. to activate the fatty acid alkyl ester as acylating agent, the ester and the alkali metal carbonate are mixed with intensive stirring. It has proved to be of advantage in this regard to carry out the activation at temperatures of 40 to 120° C. and preferably 80 to 100° C. The quantity of alkali metal carbonate used is preferably in the range from 5 to 50% by weight, based on the alkyl ester. The ester undergoes chemisorption onto the surface of the carbonate.

Glycoses

Glycoses in the context of the invention include the polyhydroxyaldehydes (aldoses) and polyhydroxyketones (ketoses) also referred to as carbohydrates and relatively high molecular weight compounds which can be converted into such substances by hydrolysis. According to the invention, both monomeric polyhydroxyaldehydes or polyhydroxyketones (monosaccharides) and their dimers to decamers (disaccharides, trisaccharides, oligosaccharides) may be used as glycoses. Suitable monosaccharides (also known as "simple sugars") are, for example, bioses, trioses, tetraoses, pentoses, hexoses, heptoses, etc. Typical examples of aldopentoses are D-ribose, D-xylose and L-arabinose. The most important aldohexoses include D-glucose, D-mannose and D-galactose while the ketohexoses include D-fructose and sorbose. The 6-deoxysugars, L-fucose and L-rhamnose, are also widely used hexoses and are also suitable as starting materials. The simplest oligosaccharides suitable as starting materials are the disaccharides. Sucrose (cane sugar, beet sugar), lactose (milk sugar) and/or maltose (malt sugar) are preferably used. According to the invention it is preferred to mono- and/or disaccharides, sucrose or glucose being particularly preferred.

Emulsifiers

According to the invention, it has proved to be of particular advantage to use carbohydrate partial esters which are identical with the target products as emulsifiers. It is particularly preferred to use sucrose partial esters with a degree of etherification of 1 to 3. Other suitable co-emulsifiers are, for example, nonionic surfactants from at least one of the following groups:

(1) products of the addition of 2 to 30 mol of ethylene oxide and/or 0 to 5 mol of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 mol of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 mol of ethylene oxide with castor oil and/or hydrogenated castor oil;

(6) polyol esters and, in particular, polyglycerol esters such as, for example, polyglycerol polyricinoleate or polyglycerol poly-12-hydroxystearate. Mixtures of compounds from several of these classes are also suitable;

(7) products of the addition of 2 to 15 mol of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) trialkyl phosphates and mono-, di- and/or tri-PEG-alkyl phosphates;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide with fatty alcohols, fatty acids, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{1/18}$ fatty acid monoesters and diesters of adducts of ethylene oxide with glycerol are known as refatting agents for cosmetic formulations from DE-PS 20 24 051. $C_{8/18}$ alkyl mono- and oligoglycosides are produced in particular by reacting glucose or oligosaccharides with primary alcohols containing 8 to 18 carbon atoms. So far as the glucoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based. According to the invention, however, it has proved to be of particular advantage to use carbohydrate partial esters identical with the target products as emulsifiers. The carbohydrate ester emulsifiers and the glycoses are used in a molar ratio of 1:6 to 6:1 and preferably 1:5 to 5:1. The percentage content of the co-emulsifiers may be in the range from 5 to 50% by weight and is preferably in the range from 10 to 25% by weight, based on the emulsifiers.

Transesterification

The transesterification is carried out by preparing an emulsion/dispersion containing the catalyst system, the glycose and the carbohydrate ester and optionally other emulsifiers with vigorous stirring. The emulsion/dispersion has a mean particle size of 10 to 60 $\mu$m and preferably 20 to 40 $\mu$m. The transesterification takes place in this emulsion/dispersion at temperatures of preferably 100 to 160° C. and more preferably 120 to 140° C. and under a reduced pressure of 1 to 10 mbar and preferably 2 to 8 mbar, the reaction times being in the range from 1 to 4 h. Any alcohol released may readily be distilled off in vacuo. Carbohydrate partial esters with a degree of esterification of preferably 1 to 6 and more preferably 1 to 3 are obtained in this way.

Commercial Applications

The carbohydrate esters obtainable by the process according to the invention have excellent surface-active properties and may be used, for example, as emulsifiers for the production of foods (bread, confectionery, ice cream, etc.) and cosmetic preparations in which they may be present in quantities of 0.1 to 10% by weight and preferably 1 to 5% by weight. The carbohydrate esters are particularly suitable as emulsifiers for the production of polyacrylic or polymethacrylic acid compounds which may be used as superadsorbers, for example for diapers. Since the emulsifiers remain in the product, not only their excellent performance properties, but also their particular dermatological compatibility is of particular relevance. Accordingly, the present invention also relates to the use of the carbohydrate esters obtainable by the process according to the invention as emulsifiers for the production of foods, cosmetic products and superadsorbers.

EXAMPLES

Example 1

47.5 g (0.2 mol) of hydrogenated palm oil fatty acid methyl ester were introduced into a 500 ml three-necked flask equipped with a high-speed stirrer, reflux condenser and dropping funnel and heated to 65° C. 5 g (0.035 mol) of potassium carbonate, corresponding to 12% by weight, based on the methyl ester, were added at a stirring speed of 1000 r.p.m. 10 g (0.02 mol) of an ester of sucrose with palm oil fatty acid (degree of esterification ca. 2) were then added in portions to the resulting dispersion through the dropping funnel. After stirring for 15 minutes, the stirring speed was increased to 2000 r.p.m. and 37.5 g(0.1 mol) of sucrose were added (molar ratio of methyl ester to sucrose=2). The resulting emulsion/dispersion was then stirred for another 4 hours at 300 r.p.m., at a temperature of 120° C. and under a reduced pressure of 7 mbar. A sucrose ester containing 15% by weight of monoester, 25% by weight of diester and 60% by weight of higher homologs, based on the quantity of carbohydrate ester, was obtained. The content of unreacted ester in the reaction mixture was below 1% by weight while the content of free sucrose was 6% by weight.

Example 2

Example 1 was repeated using 56.8 g (0.2 mol) of tallow fatty acid methyl ester, 10 g of potassium carbonate (corresponding to 18% by weight, based on methyl ester), 15 g (0.03 mol) of sucrose ester and 51.3 g (0.15 mol) of sucrose (molar ratio of methyl ester to sucrose=1.3). A sucrose ester containing 11% by weight of monoester, 29% by weight of diester and 60% by weight of higher homologs, based on the quantity of carbohydrate ester, was obtained. The content of unreacted ester in the reaction mixture was below 1% by weight while the content of free sucrose was 7% by weight.

What is claimed is:

1. A process for making carbohydrate partial esters having a degree of esterification of from 1 to 6 comprising:
    (a) providing a catalytically active mixture containing:
        (i) an alkali metal carbonate; and
        (ii) a fatty acid lower alkyl ester corresponding to formula (I):

$$R^1CO—OR^2 \qquad (I)$$

wherein $R^1CO$ is a linear or branched, saturated or unsaturated acyl group having from 6 to 22 carbon atoms, and $R^2$ is a linear or branched alkyl group containing from 1 to 5 carbon atoms;
    (b) providing an emulsifier mixture containing:
        (iii) a glycose component having from 5 to 12 carbon atoms; and
        (iv) a carbohydrate partial ester; and
    (c) combining the catalytically active mixture with the emulsifier mixture, with vigorous stirring, to form an emulsion/dispersion containing particles having a mean diameter of from 10 to 60 μm.

2. The process of claim 1 wherein the alkali metal carbonate is selected from the group consisting of sodium carbonate, potassium carbonate, and mixtures thereof.

3. The process of claim 1 wherein in formula (I), $R^2$ is a methyl group, an ethyl group, or both.

4. The process of claim 1 wherein the catalytically active mixture is prepared at a temperature of from 40 to 120° C., with intensive stirring.

5. The process of claim 1 wherein the glycose component is selected from the group consisting of monosaccharides, disaccharides, and mixtures thereof.

6. The process of claim 1 wherein the carbohydrate partial ester is a sucrose partial ester having a degree of esterefication of from 1 to 3.

7. The process of claim 1 wherein the catalytically active mixture and the emulsifier mixture are combined at a temperature of from 100 to 160° C., and a reduced pressure of from 1 to 10 mbar.

8. The process of claim 1 wherein the alkali metal carbonate is used in an amount of from 5 to 50% by weight, based on the weight of the fatty acid lower alkyl ester.

9. The process of claim 1 wherein the process is conducted in the absence of any solvents.

10. The process of claim 1 wherein the glycose component and carbohydrate partial ester are employed in a molar ratio of from 1:6 to 6:1.

* * * * *

UNITED STATES PATENT AND TRADEMARK OFFICE
CERTIFICATE OF CORRECTION

PATENT NO. : 6,706,877 B1
DATED : March 16, 2004
INVENTOR(S) : Claverie et al.

It is certified that error appears in the above-identified patent and that said Letters Patent is hereby corrected as shown below:

Title page,
Item [*] Notice, delete "215" and insert -- 825 --.

Signed and Sealed this

Twenty-third Day of August, 2005

JON W. DUDAS
*Director of the United States Patent and Trademark Office*